United States Patent [19]

Betzing et al.

[11] 4,341,790
[45] Jul. 27, 1982

[54] PYRROLIDINYLALKYLCARBOXYLIC ACID AMIDE DERIVATIVES, THEIR PREPARATION AND PHARMACEUTICAL COMPOSITIONS CONTAINING THEM

[75] Inventors: Hans Betzing, Kerpen-Horrem; Jürgen Biedermann, Pulheim-Stommel; Carsten Materne, Bonn; Volker Neuser, Bergheim-Ahe, all of Fed. Rep. of Germany

[73] Assignee: A. Nattermann & Cie. GmbH, Fed. Rep. of Germany

[21] Appl. No.: 155,952

[22] Filed: Jun. 3, 1980

[30] Foreign Application Priority Data

Jun. 13, 1979 [DE] Fed. Rep. of Germany ....... 2923975
Jun. 13, 1979 [DE] Fed. Rep. of Germany ....... 2924011

[51] Int. Cl.³ .................... A61K 31/40; A61K 31/44; C07D 207/27; C07D 207/273
[52] U.S. Cl. .............................. 424/274; 260/326.25; 260/326.43; 424/263; 546/281
[58] Field of Search ...................... 260/326.25, 326.43; 546/281; 424/263, 274

[56] References Cited

U.S. PATENT DOCUMENTS

| 2,778,834 | 1/1957 | Bruce et al. | 260/326.43 |
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |

FOREIGN PATENT DOCUMENTS

| 2106418 | 8/1971 | Fed. Rep. of Germany | 260/326.43 |
| 1039113 | 8/1966 | United Kingdom | 260/326.43 |

OTHER PUBLICATIONS

Albertson, Organic Reactions, vol. 12, (Adams et al., ed., New York, 1962), pp. 205–213.

Primary Examiner—Alton D. Rollins
Attorney, Agent, or Firm—Burns, Doane, Swecker & Mathis

[57] ABSTRACT

2-Oxo-1-pyrrolidinylalkylcarboxylic acid amides of formula I

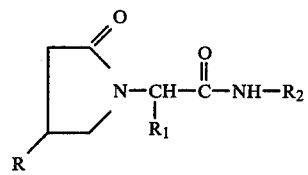

in which R represents a hydrogen atom or hydroxy group, $R_1$ represents a hydrogen atom or a methyl group and $R_2$ represents a substituted or unsubstituted pyridyl group or a substituted phenyl group, the substitution being by from 1 to 3 substituents, which may be the same or different selected from halogen atoms, trifluoromethyl, nitro and acetyl groups, straight or branched-chain alkyl groups having 1–4 carbon atoms, alkoxy groups having 1–4 carbon atoms, straight or branched-chain alkylmercapto groups having 1–7 carbon atoms, substituted alkylmercapto groups of the general formula II

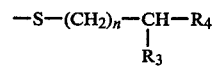

in which n represents 1 or 2, $R_3$ is a hydrogen atom or a methyl group and $R_4$ is a hydroxy group or an amino group of the general formula V

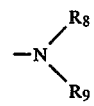

in which $R_8$ represents a hydrogen atom or methyl group and $R_9$ represents a methyl group or substituted or unsubstituted benzyl group, or $R_8$ and $R_9$ together with the nitrogen atom shown in formula V, form a substituted pyrrolidine ring; sulphonyl groups of the general formula III

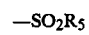

in which $R_5$ represents an —$NH_2$ group or an alkyl group having 1–3 carbon atoms; and aminoethoxycarbonyl groups of the general formula IV

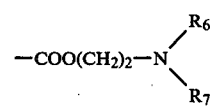

in which each of $R_6$ and $R_7$, which may be the same or different, represents a hydrogen atom or methyl or ethyl group; and the pharmaceutically tolerable acid addition salts of compounds of formula I having a basic nitrogen atom are useful in treating cerebral circulatory disturbances, cerebro-atrophic crises and cerebral ageing processes.

6 Claims, No Drawings

PYRROLIDINYLALKYLCARBOXYLIC ACID AMIDE DERIVATIVES, THEIR PREPARATION AND PHARMACEUTICAL COMPOSITIONS CONTAINING THEM

The invention relates to new 2-oxo-1-pyrrolidinylalkylcarboxylic acid amides which exhibit valuable pharmacological properties since, inter alia, they improve the circulation of blood in the cerebral region and thus improve the supply of blood to the brain.

The compounds of the invention are of the general formula I

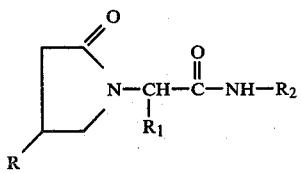

in which R represents a hydrogen atom or hydroxy group, $R_1$ represents a hydrogen atom or a methyl group and $R_2$ represents a substituted or unsubstituted pyridyl group or a substituted phenyl group, the substitution being by from 1 to 3 substituents, which may be the same or different, selected from halogen atoms, trifluoromethyl, nitro and acetyl groups, straight- or branched-chain alkyl groups having 1-4 carbon atoms, alkoxy groups having 1-4 carbon atoms, straight- or branched-chain alkylmercapto groups having 1-7 carbon atoms, substituted alkylmercapto groups of the general formula II

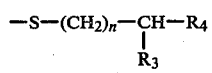

in which n represents 1 or 2, $R_3$ is a hydrogen atom or a methyl group, and $R_4$ is a hydroxy group or an amino group of the general formula V

in which $R_8$ represents a hydrogen atom or methyl group and $R_9$ represents a methyl group or substituted or unsubstituted benzyl group, or $R_8$ and $R_9$, together with the nitrogen atom shown in formula V, form a substituted pyrrolidine ring; sulphonyl groups of the general formula III

in which $R_5$ represents an $-NH_2$ group or an alkyl group having 1-3 carbon atoms; and aminoethoxycarbonyl groups of the general formula IV

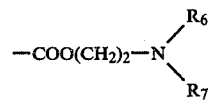

in which each of $R_6$ and $R_7$, which may be the same or different, represents a hydrogen atom or methyl or ethyl group; and the pharmaceutically tolerable acid addition salts of compounds of formula I having a basic nitrogen atom.

Examples of the substituents on the pyridyl or phenyl group are chlorine and fluorine atoms; methyl, ethyl, n-propyl, isopropyl, sec-butyl and n-butyl groups; methoxy and isopropoxy groups; methylmercapto, n-propylmercapto, isopropylmercapto, sec.-butylmercapto and n-heptylmercapto groups; 2-hydroxypropylmercapto, 3-(N,N-dimethylamino)-propylmercapto and 2-(N-methyl-N-benzylamino)-ethylmercapto groups; N-methyl-N-benzylaminoalkylmercapto groups of formula II in which the benzyl group is substituted by methoxy group(s), especially a 2-(N-methyl-N-(3,4-dimethoxybenzyl)-amino)-ethylmercapto group; 1-pyrrolidinylalkylmercapto groups of formula II in which the pyrrolidine ring of $R_2$ is substituted by a 2-oxo group, especially a 2-(2-oxo-1-pyrrolidinyl)-ethylmercapto group; and a 2-(N,N-diethylamino)-ethoxycarbonyl group. Conveniently the pyridyl group is unsubstituted. It will usually be attached by its 2-, 3- or 4-carbon atom to the right-hand nitrogen atom in formula I.

The new compounds of the formula I can be prepared in accordance with the invention by reacting a 2-oxo-1-pyrrolidinylalkylcarboxylic acid of the general formula VI

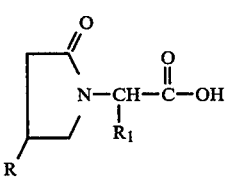

in which R and $R_1$ have the meaning indicated above, or a reactive derivative thereof, with an amine of the formula VII

in which $R_2$ has the meaning indicated above, together with N,N'-dicyclohexylcarbodiimide in an organic solvent, e.g. chloroform, methylene chloride, tetrahydrofuran, acetonitrile or ethyl acetate, at a temperature between 0° C. and the boiling point of the particular solvent, usually 0° to 80° C. The desired compound of formula I is separated from the resultant N,N'-dicyclohexylurea.

Suitable reactive derivatives of the acids of formula VI for preparing amides, are those of a kind which are in general known, for example mixed anhydrides obtained using chloroformic acid esters, activated esters, for example nitrophenyl esters, cyanomethyl esters or trichlorophenyl esters, and acid chlorides.

The compounds of the general formula I in which R represents an OH group and/or $R_1$ represents a methyl group have one and/or two asymmetric carbon atoms. The invention includes these compounds in the form of racemates and optically active isomers in each case. The resolution of the racemates can be effected by processes known per se, through the formation of diastereomeric salts.

Compounds of formula I having a basic nitrogen atom, principally those having an amino-substituent as specified, form acid addition salts, which can be prepared in manner known per se from the free base.

The compounds according to the invention possess valuable pharmacological properties. They exhibit central vaso-active properties and properties for regulating metabolism and inhibiting the aggregation of thrombocytes and are suitable, above all, for the treatment of diseases of the cerebro-ischaemic and atrophic type, including organic psychosyndrome and migraine. The compounds also exhibit good tranquillising properties for many patients.

The pharmacoprophylaxis and therapy of diseases resulting from inadequate cerebral circulation, cerebroatrophic crises and cerebral ageing processes are nowadays becoming increasingly important and there has hitherto been no lack of attempts to find vasotropic compounds and compounds for regulating the metabolism which have a desirable effect on the diseases mentioned here. However, it has not been possible to achieve a decisive improvement by means of medicinal treatment with nootropic agents, central vasotropic agents and other therapeutic agents. The new active compounds now make it possible to treat these diseases.

A preferred class of compounds of the invention is those wherein $R_2$ represents a phenyl radical substituted by methyl radicals in the 2- and 6-positions. 2-Oxo-1-pyrrolidinylacetic acid-2,6-dimethylanilide, which combines vaso-active properties and properties for regulating metabolism which make it suitable for the treatment of cerebral circulatory disturbances, cerebro-atrophic crises and cerebral ageing processes and other cerebral affections, has been shown to be particularly effective. This is the more surprising since 2-oxo-1-pyrrolidinylacetic acid anilide, which has a similar structure and is known from British Patent Specification No. 1,039,113, exhibits none of these effects. The 2,6-dimethylanilide can easily be prepared from 2-oxo-1-pyrrolidinylacetic acid by the above-described method.

The following methods have been used to investigate the pharmacodynamic properties of the compounds according to the invention:

1. Prolongation of cerebral survival time under hypoxaemia caused by $NaNO_2$.

Starting from the results of Gibson and Blass (J. Neurochemistry 27, 1976), a cerebral hypoxia is produced in male mice by means of $NaNO_2$ (225 mg/kg, subcutaneous). The cerebral hypoxia period is marked by a characteristic spasmodic behaviour and ends in the death of the experimental animals. Measurements are made to determine whether the survival time under cerebrohypoxic conditions is significantly prolonged by premedication.

2. Prolongation of the cerebral survival time in the case of hypoxaemia caused by sub-atmospheric pressure.

It is known that animals exhibit a characteristic neuropathological behaviour if the oxygen pressure is reduced. This neuropathological behaviour is induced in male mice by a progressive reduction of the pressure to 26.66 kPa in an observation chamber and is used as an indicator of the cerebral hypoxia period. It ends in the death of the experimental animal. An investigation is made to determine whether the survival time under cerebro-hypoxic conditions is prolonged significantly by premedication.

3. Protection against amnesia induced by electric shock.

Starting from the results of Taber and Banuazizi (Psychopharmakologia 9, 1966), male mice are taught not to enter a certain compartment of the cage in order to avoid an electric shock. The response is extinguished by means of an electric shock administered via head electrodes (electric shock amnesia).

An investigation is made to determine whether the dwell time in the compartment of the cage which is free from electric shocks is significantly prolonged, as a measure of the memory of the experimental animals, by premedication.

The following commercially available compounds were used in all the tests: papaverine, cinnarizine, meclofenoxate, piracetam, vincamine, propranolol, pyritinol and 2-oxo-1-pyrrolidinylacetic acid anilide.

In the Table 1 which follows, the pharmacologically effective properties of the compounds according to the invention, determined by the experimental methods mentioned above, are compared with the commercially available compounds.

TABLE 1

| Compound | Mode of administration | $NaNO_2$— hypoxaemia | Sub-atmospheric pressure hypoxaemia | Amnesia |
|---|---|---|---|---|
| DZL 221[1] | oral | + | + | + |
| PA[2] | oral | — | — | — |
| Papaverine | intravenous | + | — | — |
| Cinnarizine | oral | — | — | — |
| Meclofenoxate | oral | — | — | — |
| Piracetam | oral | — | + | + |
| Vincamine | oral | — | + | + |
| Propranol | oral | + | — | + |
| Pyritinol | oral | — | — | + |

As can be seen from Table 1, the compound of the invention exhibits a completely novel pattern of action in cerebral protection, since, in contrast to the known compounds, it is effective in all three test procedures.

The compound of Example 6 is highly active, well tolerated and has a very low toxicity:

$LD_{50}$: 1,766 mg/kg—mice, administered orally $LD_{50}$: 421 mg/kg—mice, administered intravenously Its excellent activity and good toleration, together with its effect of inhibiting aggregation of thrombocytes, make the compound of Example 6 outstandingly suitable for the treatment of diseases of the cerebro-ischaemic and cerebro-atrophic type, including organic pyscho-syndrome and migraine. In addition, the compound has good tranquillising properties.

The invention includes pharmaceutical compositions comprising a compound of the invention and a pharmaceutically acceptable excipient. These compositions can take any form, e.g. tablets, capsules, dragees, pills, emulsions, suspensions and solutions, using a pharmaceutically suitable excipient (which term includes a solvent or carrier).

The following are Examples of excipients which can be used: non-toxic organic solvents, such as vegetable oils (for example groundnut oil or soya oil), alcohols (for example polyethylene glycol or glycerol), solid excipients, such as, for example, ground minerals (kaolins, talc or silicates), sugars (for example lactose or glucose), emulsifiers (for example fatty acid esters or fatty alcohol ethers), dispersing agents (for example methylcellulose or starch) and lubricants (for example talc, stearic acid or cocoa butter).

Administration is usually carried out enterally using doses of 1–1,000 mg, preferably 10–100 mg, or parenterally using doses of 0.1–100 mg, particularly 1–20 mg.

The preparation of the compounds of the invention is illustrated in greater detail by means of the following Examples:

EXAMPLE 1

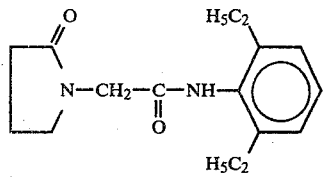

2-Oxo-1-pyrrolidinylacetic acid 2,6-diethylanilide 22.9 g (0.16 mol) of 2-oxo-1-pyrrolidinylacetic acid $C_6H_9NO_3$ [143.1] and 23.9 g (0.16 mol) of 2,6-diethylaniline $C_{10}H_{15}N$ [149.2] are heated under reflux for 4 hours in 160 ml of absolute chloroform together with 33.0 g (0.16 mol) of N,N'-dicyclohexylcarbodiimide $C_{13}H_{22}N_2$ [206.3]. After cooling, the precipitated N,N'-dicyclohexylurea is filtered off, the filtrate is concentrated and the residue is recrystallised.

Yield: 12.4 g (28.3% of theory) $C_{16}H_{22}N_2O_2$ [274.4]
Melting point: 195° C. (methanol/water)

EXAMPLE 2

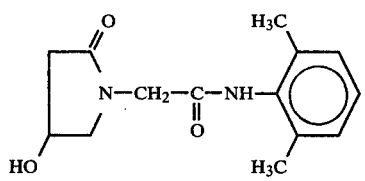

4-Hydroxy-2-oxo-1-pyrrolidinylacetic acid 2,6-dimethylanilide 19.1 g (0.12 mol) of 4-hydroxy-2-oxo-1-pyrrolidinylacetic acid $C_6H_9NO_4$ [159.1] and 14.5 g (0.12 mol) of 2,6-dimethylaniline $C_8H_{11}N$ [121.2] are heated under reflux for 3 hours in 120 ml of absolute chloroform together with 24.8 g (0.12 mol) of N,N'-dicyclohexylcarbodiimide $C_{13}H_{22}N_2$ [206.3]. After cooling, the precipitated N,N'-dicyclohexylurea is filtered off, the filtrate is concentrated in vacuo and the residue is recrystallised.

Yield: 11.5 g (36.4% of theory) $C_{14}H_{18}N_2O_3$ [262.3]
Melting point: 159° C. (ethyl acetate/ether).

EXAMPLE 3

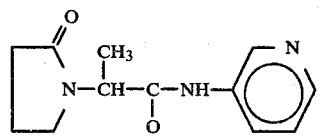

2-[2-Oxo-1-pyrrolidinyl]propionic acid N-3-pyridylamide 36.1 g (0.23 mol) of 2-[2-oxo-1-pyrrolidinyl]-propionic acid $C_7H_{11}NO_3$ [157.1] and 21.6 g (0.23 mol) of 3-aminopyridine $C_5H_6N_2$ [94.1] are heated under reflux for 4 hours in 230 ml of absolute chloroform together with 47.4 g (0.23 mol) of N,N'-dicyclohexylcarbodiimide $C_{13}H_{22}N_2$ [206.3]. After cooling, the precipitated N,N'-dicyclohexylurea is filtered off, the filtrate is concentrated (in vacuo) and the residue is recrystallised.

Yield: 26.0 g (48.5% of theory) $C_{12}H_{15}N_3O_2$ [233.3]
Melting point: 108°–109° C. (ethyl acetate/diisopropyl ether).

EXAMPLE 4

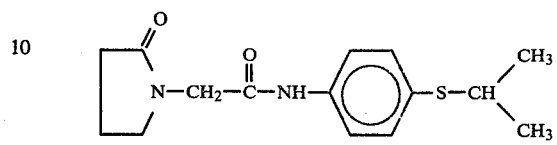

2-Oxo-1-pyrrolidinylacetic acid 4-isopropylmercapto anilide 14.3 g (0.1 mol) of 2-oxo-1-pyrrolidinylacetic acid $C_6H_9NO_3$ [143.1] and 16.7 g (0.1 mol) of 4-isopropylmercaptoaniline $C_9H_{13}N_5$ [167.3] are heated under reflux for 3 hours in 100 ml of absolute chloroform together with 20.6 g (0.1 mol) of N,N'-dicyclohexylcarbodiimide $C_{13}H_{22}N_2$ [206.3]. After cooling, the precipitated N,N'-dicyclohexylurea is filtered off, the filtrate is concentrated and the residue is recrystallised.

Yield: 11.7 g (40% of theory) $C_{15}H_{20}N_2O_2$ S [292.2]
Melting point: 128° C. (ethanol)

EXAMPLE 5

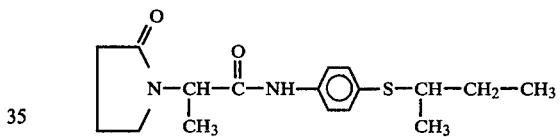

2-[2-oxo-1-pyrrolidinyl]-propionic acid 4-(2-butylmercapto)-anilide 15.7 g (0.1 mol) of 2-[2-oxo-1-pyrrolindyl]-propionic acid $C_7H_{11}NO_3$ [157.1] and 18.3 g (0.1 mol) of 4-sec.-butylmercaptoaniline $C_{10}H_{15}NS$ [181.3] are heated under reflux for 4 hours in 100 ml of absolute chloroform together with 20.6 g (0.1 mol) of N,N'-dicyclohexylcarbodiimide $C_{13}H_{22}N_2$ [206.3]. After cooling, the precipitated N,N'-dicyclohexylurea is filtered off, the filtrate is concentrated and the residue is recrystallised.

Yield: 16 g (50% of theory) of $C_{17}H_{24}N_2O_2S$ [320.4]
Melting point: 87° C. (ethanol)

EXAMPLE 6

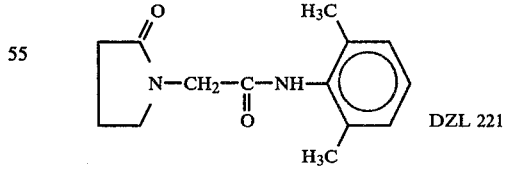

DZL 221

2-Oxo-1-pyrrolidinylacetic acid, 2,6-dimethylanilide 14.3 g (0.1 mol) of 2-oxo-1-pyrrolidinylacetic acid $C_6H_9NO_3$ [143.1] and 12.1 g (0.1 mol) of 2,6-dimethylaniline $C_8H_{11}N$ [121.2] are heated under reflux for 3 hours in 100 ml of absolute chloroform together with 20.6 g (0.1 mol) of N,N'-dicyclohexylcarbodiimide $C_{13}H_{22}N_2$ [206.3]. After cooling, the precipitated N,N'- dicyclohexylurea is filtered off, the filtrate is concentrated and the residue is recrystallised.

Yield. 18.7 g (76% of theory) $C_{14}H_{18}N_2O_2$ [246.3]

Melting point: 153° C. (water)

Elementary analysis: $C_{14}H_{18}N_2O_2$ [246.3]—Calculated: C=68.27%, H=7.37%, N=11.37%, O=12.99%. Found: C=68.12%, H=7.37%, N=11.39%, O=12.94%; C=68.09%, H=7.42%, N=11.34%, O=13.09%.

IR spectrum: Instrument: Perkin-Elmer model 257 (KBr): $\eta_{NH}$:3260 cm$^{-1}$, $\eta_{CO\ (ring\ and\ amide)}$:1650–1700 cm$^{-1}$ (overlapping bands)

$^1$H-NMR spectrum: Instrument: Hitachi Perkin-Elmer, 60 MHz, model R-24 Solvent: CDCl$_3$ (TMS as internal standard δ=0) NH 7.85 (s), CH$_{aromatic}$ 7.0 (s), CH$_2$ 4.1 (s), CH$_2$ 3.6 (t), CH$_2$—CH$_2$ 2.2 (m), CH$_2$ 2.1 (s).

Mass spectrum: Instrument: 311 A Varian Mat; electron energy 70eV, 200 A, temperature of source of ions 200° C., solid sample vaporisation or gas inlet for the reference substance (PFK), scanning control and recording and processing of data via a Finnigan-Incos system; M+: m/e 246 (60%).

Thin layer chromatography: 60 F$_{254}$ silica gel prepared thin layer chromatographic plates (Merck)

Spraying reagent: Bromocresol Green (0.05% strength, Merck) R$_f$=0.83

Eluant: chloroform/methanol/25% strength ammonia 70:26:4 (V/V/V) R$_f$=0.36

Eluant: chloroform/methanol 90:10 (V/V)

Other compounds of formula I were prepared, and their melting points determined, analogously to the procedures of Examples 1 to 6. Table 2 lists these compounds together with those of Examples 1 and 3 to 5.

TABLE 2

$$\underset{R_1}{\underset{|}{N-CH}}-\overset{O}{\overset{\|}{C}}-NH-R_2$$

(with N in a ring bearing a C=O)

| No. | R$_1$ | R$_2$ | Empirical formula | Molecular weight | Melting point °C. | Yield % |
|-----|-------|-------|-------------------|------------------|-------------------|---------|
| 1 | —H | —⟨○⟩—CH$_3$ | C$_{13}$H$_{16}$N$_2$O$_2$ | 232.3 | 134 | 50 |
| 2 | —CH$_3$ | —⟨○⟩—CH$_3$ | C$_{14}$H$_{18}$N$_2$O$_2$ | 246.3 | 140 | 74 |
| 3 | —H | —⟨○⟩—CH$_2$—CH$_3$ | C$_{14}$H$_{18}$N$_2$O$_2$ | 246.3 | 150 | 35 |
| 4 | —CH$_3$ | —⟨○⟩—CH$_2$—CH$_3$ | C$_{15}$H$_{20}$N$_2$O$_2$ | 260.3 | 129 | 81 |
| 5 | —H | —⟨○⟩—CH$_2$—CH$_2$—CH$_3$ | C$_{15}$H$_{20}$N$_2$O$_2$ | 260.3 | 140 | 30 |
| 6 | —H | H$_3$C-⟨○⟩- (ortho) | C$_{13}$H$_{16}$N$_2$O$_2$ | 232.3 | 119 | 36 |
| 7 | —H | —⟨○⟩—CH(CH$_3$)$_2$ | C$_{15}$H$_{20}$N$_2$O$_2$ | 260.3 | 135 | 56 |
| 8 | —CH$_3$ | —⟨○⟩—CH(CH$_3$)$_2$ | C$_{16}$H$_{22}$N$_2$O$_2$ | 274.4 | 109 | 58 |
| 9 | —H | —⟨○⟩—CH$_2$—CH$_2$—CH$_2$—CH$_3$ | C$_{16}$H$_{22}$N$_2$O$_2$ | 274.4 | 102 | 28 |
| 10 | —CH$_3$ | —⟨○⟩—CH$_2$—CH$_2$—CH$_2$—CH$_3$ | C$_{17}$H$_{24}$N$_2$O$_2$ | 288.4 | 110 | 70 |
| 11 | —H | —⟨○⟩—CH(CH$_3$)—CH$_2$—CH$_3$ | C$_{16}$H$_{22}$N$_2$O$_2$ | 274.4 | 123 | 30 |

TABLE 2-continued

[Structure shown at top of table: pyrrolidinone ring with N-CH(R₁)-C(=O)-NH-R₂]

| No. | R₁ | R₂ | Empirical formula | Molecular weight | Melting point °C. | Yield % |
|-----|-----|-----|-------------------|------------------|-------------------|---------|
| 12 | —H | 4-methoxyphenyl | $C_{13}H_{16}N_2O_3$ | 248.3 | 130 | 48 |
| 13 | —CH₃ | 4-methoxyphenyl | $C_{14}H_{18}N_2O_3$ | 262.3 | 138 | 45 |
| 14 | —H | 3,4-dimethoxyphenyl | $C_{14}H_{18}N_2O_4$ | 278.2 | 142 | 60 |
| 15 | —CH₃ | 3,4-dimethoxyphenyl | $C_{15}H_{20}N_2O_4$ | 292.3 | 170 | 22 |
| 16 | —H | 2,4-dimethoxyphenyl | $C_{14}H_{18}N_2O_4$ | 278.3 | 158 | 45 |
| 17 | —CH₃ | 2,4-dimethoxyphenyl | $C_{15}H_{20}N_2O_4$ | 292.3 | 101 | 39 |
| 18 | —H | 2,3,4-trimethoxyphenyl | $C_{15}H_{20}N_2O_5$ | 308.3 | 145 | 15 |
| 19 | —CH₃ | 2,3,4-trimethoxyphenyl | $C_{16}H_{22}N_2O_5$ | 322.4 | 164 | 12 |
| 20 | —H | 2,5-dimethylphenyl | $C_{14}H_{18}N_2O_2$ | 246.3 | 140 | 30 |
| 21 | —CH₃ | 2,5-dimethylphenyl | $C_{15}H_{20}N_2O_2$ | 260.3 | 120 | 38 |
| 22 | —H | 3,4-dimethylphenyl | $C_{14}H_{18}N_2O_2$ | 246.3 | 150 | 30 |
| 23 | —CH₃ | 3,4-dimethylphenyl | $C_{15}H_{20}N_2O_2$ | 260.3 | 109 | 65 |

TABLE 2-continued $$\underset{R_1}{\overset{\displaystyle\mathop{N-CH-C-NH-R_2}\limits^{\displaystyle O\atop\|}}{\bigg(}}$$

| No. | $R_1$ | $R_2$ | Empirical formula | Molecular weight | Melting point °C. | Yield % |
|---|---|---|---|---|---|---|
| 24 | —H | 2,6-dimethylphenyl | $C_{14}H_{18}N_2O_2$ | 246.3 | 146 | 30 |
| 25 | —CH₃ | 2,6-dimethylphenyl | $C_{15}H_{20}N_2O_2$ | 260.3 | 96 | 26 |
| 26 (Ex. 1) | —H | 2,6-diethylphenyl | $C_{16}H_{22}N_2O_2$ | 274.4 | 195 | 28 |
| 27 | —H | 2,4,6-trimethylphenyl | $C_{15}H_{20}N_2O_2$ | 260.3 | 173 | 38 |
| 28 | —CH₃ | 2,4,6-trimethylphenyl | $C_{16}H_{22}N_2O_2$ | 274.4 | 129 | 42 |
| 29 | —H | 2-methyl-4-methoxyphenyl | $C_{14}H_{18}N_2O_3$ | 262.3 | 142 | 35 |
| 30 | —CH₃ | 2-methyl-4-methoxyphenyl | $C_{15}H_{20}N_2O_3$ | 276.3 | 114 | 50 |
| 31 | —H | 2-methoxy-5-methylphenyl | $C_{14}H_{18}N_2O_3$ | 262.3 | 134 | 32 |
| 32 | —CH₃ | 2-methoxy-5-methylphenyl | $C_{15}H_{20}N_2O_3$ | 276.3 | 89 | 54 |
| 33 | —H | 2-methyl-4-chlorophenyl | $C_{13}H_{15}ClN_2O_2$ | 266.7 | 144 | 30 |

TABLE 2-continued

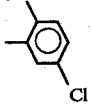

| No. | R₁ | R₂ | Empirical formula | Molecular weight | Melting point °C. | Yield % |
|---|---|---|---|---|---|---|
| 34 | —CH₃ | H₃C— ⌬ —Cl (2-Me, 4-Cl) | $C_{14}H_{17}ClN_2O_2$ | 280.8 | 134 | 70 |
| 35 | —H | H₃C— ⌬ —Cl | $C_{13}H_{15}ClN_2O_2$ | 266.7 | 140 | 35 |
| 36 | —CH₃ | H₃C— ⌬ —Cl | $C_{14}H_{17}ClN_2O_2$ | 280.8 | 127 | 58 |
| 37 | —H | Cl, H₃C substituted phenyl | $C_{13}H_{15}ClN_2O_2$ | 266.7 | 142 | 20 |
| 38 | —CH₃ | Cl, H₃C substituted phenyl | $C_{14}H_{17}ClN_2O_2$ | 280.8 | 103 | 14 |
| 39 | —H | Cl, H₃CO substituted phenyl | $C_{13}H_{15}ClN_2O_3$ | 282.7 | 126 | 40 |
| 40 | —CH₃ | Cl, H₃CO substituted phenyl | $C_{14}H_{17}ClN_2O_3$ | 296.7 | 111 | 35 |
| 41 | —H | F, H₃C substituted phenyl | $C_{13}H_{15}FN_2O_2$ | 250.2 | 120 | 30 |
| 42 | —CH₃ | F₃C substituted phenyl | $C_{14}H_{15}F_3N_2O_2$ | 300.3 | 82 | 18 |
| 43 | —H | ⌬—O—CH(CH₃)₂ | $C_{15}H_{20}N_2O_3$ | 276.3 | 142 | 50 |
| 44 | —H | ⌬—C(O)—O—CH₂—CH₂—N(C₂H₅)₂ | $C_{19}H_{27}N_3O_4$ | 361.4 | 117 | 13 |

TABLE 2-continued

[structure: lactam-N-CH(R₁)-C(=O)-NH-R₂]

| No. | R₁ | R₂ | Empirical formula | Molecular weight | Melting point °C. | Yield % |
|---|---|---|---|---|---|---|
| 45 | —H | H₃CO—(phenyl with OCH₃ and Cl) | C₁₄H₁₇ClN₂O₄ | 312.3 | 158 | 55 |
| 46 | —CH₃ | (3-acetylphenyl) | C₁₅H₁₈N₂O₃ | 274.3 | 168 | 30 |
| 47 | —CH₃ | (3-nitrophenyl) | C₁₃H₁₅N₃O₄ | 277.3 | 153 | 10 |
| 48 | —H | (4-acetylphenyl) | C₁₄H₁₆N₂O₃ | 260.3 | 198 | 65 |
| 49 | —CH₃ | (4-acetylphenyl) | C₁₅H₁₈N₂O₃ | 274.3 | 165 | 18 |
| 50 | —H | (4-SCH₃-phenyl) | C₁₃H₁₆N₂O₂S | 264.3 | 140 | 45 |
| 51 | —CH₃ | (4-SCH₃-phenyl) | C₁₄H₁₈N₂O₂S | 278.3 | 148 | 34 |
| 52 | —H | (3-SCH₃-phenyl) | C₁₃H₁₆N₂O₂S | 264.3 | 140 | 51 |
| 53 | —CH₃ | (3-SCH₃-phenyl) | C₁₄H₁₈N₂O₂S | 278.3 | 100 | 56 |
| 54 | —H | (4-S-CH₂-CH₂-CH₃-phenyl) | C₁₅H₂₀N₂O₂S | 292.2 | 124 | 30 |
| 55 | —CH₃ | (4-S-CH₂-CH₂-CH₃-phenyl) | C₁₆H₂₂N₂O₂S | 306.4 | 122 | 54 |
| 56 (Ex. 4) | —H | (4-S-CH(CH₃)₂-phenyl) | C₁₅H₂₀N₂O₂S | 292.2 | 128 | 40 |
| 57 | —CH₃ | (4-S-CH(CH₃)₂-phenyl) | C₁₆H₂₂N₂O₂S | 306.4 | 142 | 45 |
| 58 | —H | (4-S-C(CH₃)(CH₂CH₃)-phenyl) | C₁₆H₂₂N₂O₂S | 306.4 | 110 | 35 |

TABLE 2-continued

Structure: pyrrolidinone-N-CH(R₁)-C(=O)-NH-R₂

| No. | R₁ | R₂ | Empirical formula | Molecular weight | Melting point °C. | Yield % |
|---|---|---|---|---|---|---|
| 59 (Ex. 5) | —CH₃ | —C₆H₄—S—CH(CH₃)—CH₂—CH₃ | C₁₇H₂₄N₂O₂S | 320.4 | 87 | 50 |
| 60 | —H | —C₆H₄—S—CH₂—CH(OH)—CH₃ | C₁₅H₂₀N₂O₃S | 308.4 | 128 | 35 |
| 61 | —H | —C₆H₄—S—CH₂—CH₂—N(CH₃)—CH₂—C₆H₅ | C₂₂H₂₇N₃O₂S | 397 | 91 | 30 |
| 62 | —H | —C₆H₄—S—CH₂—CH₂—N(CH₃)—CH₂—C₆H₃(OCH₃)₂ | C₂₄H₃₁N₃O₄S | 457.5 | 93 | 28 |
| 63 | —H | —C₆H₄—S—CH₂—CH₂—CH₂—N(CH₃)₂ | C₁₇H₂₅N₃O₂S | 335.3 | 120 | 35 |
| 64 | —H | —C₆H₄—S—CH₂—CH₂—N(2-oxopyrrolidinyl) | C₁₈H₂₃N₃O₃S | 361 | 115 | 22 |
| 65 | —H | —C₆H₄—SO₂—CH(CH₃)₂ | C₁₅H₂₀N₂O₄S | 324.3 | 145 | 35 |
| 66 | —H | —C₆H₄—SO₂—NH₂ | C₁₂H₁₅N₃O₄S | 297.3 | 173 | 40 |
| 67 | —H | (CH₃)₂CH—S—C₆H₅ | C₁₅H₂₀N₂O₂S | 292.4 | — | 15 |
| 68 | —H | —C₆H₄—S—(CH₂)₆—CH₃ | C₁₉H₂₈N₂O₂S | 348.5 | 108 | 30 |
| 69 | —H | pyridyl | C₁₁H₁₃N₃O₂ | 219.2 | 135 | 40 |
| 70 (Ex. 3) | —CH₃ | pyridyl | C₁₂H₁₅N₃O₂ | 233.3 | 108 | 48 |
| 71 | —CH₃ | pyridyl | C₁₂H₁₅N₃O₂ | 233.3 | 144 | 20 |
| 72 | —H | 2,6-dichlorophenyl | C₁₂H₁₂Cl₂N₂O₂ | 287.2 | 162 | 12 |

TABLE 2-continued

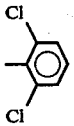

| No. | $R_1$ | $R_2$ | Empirical formula | Molecular weight | Melting point °C. | Yield % |
|---|---|---|---|---|---|---|
| 73 | —CH₃ | 2,6-Cl₂-C₆H₃ | $C_{13}H_{14}Cl_2N_2O_2$ | 301.2 | 110 | 13 |
| 74 | —H | 2,6-F₂-C₆H₃ | $C_{12}H_{12}F_2N_2O_2$ | 254.2 | 138 | 11 |
| 75 | —CH₃ | 2,6-F₂-C₆H₃ | $C_{13}H_{14}F_2N_2O_2$ | 268.3 | 99 | 9 |

We claim:

1. 2-oxo-1-pyrrolidinylalkylcarboxylic acid amides of the general formula I

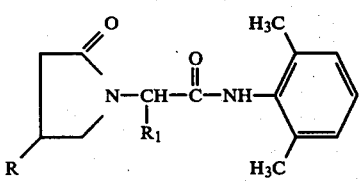

in which R is selected from the group consisting of hydrogen and hydroxyl and $R_1$ is selected from the group consisting of hydrogen and methyl, and the pharmaceutically tolerable acid addition salts of compounds of formula I having a basic nitrogen atom.

2. Compounds according to claim 1 wherein R is hydrogen.

3. As a compound according to claim 1, 2-oxo-1-pyrrolidinylacetic acid 2,6-dimethylanilide.

4. As a compound according to claim 1, 4-hydroxy-2-oxo-1-pyrrolidinylacetic acid 2,6-dimethylanilide.

5. A pharmaceutical composition for the treatment of cerebral circulatory disturbances, comprising in a therapeutically effective amount at least one compound defined in any one of claims 1, 3, or 4 and a pharmaceutically acceptable excipient.

6. A method of treating a patient for cerebral circulatory disturbance, which comprises administering to the patient a therapeutically effective dose of at least one compound defined in any one of claims 1, 4 or 5.

* * * * *